United States Patent [19]

Kresge et al.

[11] Patent Number: 5,258,566
[45] Date of Patent: Nov. 2, 1993

[54] PROCESS FOR PREPARING LONG CHAIN ALKYLAROMATIC COMPOUNDS

[75] Inventors: Charles T. Kresge, West Chester, Pa.; Quang N. Le, Cherry Hill, N.J.; Wieslaw J. Roth, Sewell, N.J.; Robert T. Thomson, Lawrenceville, N.J.

[73] Assignee: Mobil Oil Corp., Fairfax, Va.

[21] Appl. No.: 878,277

[22] Filed: May 4, 1992

[51] Int. Cl.$^5$ ................................. C07C 2/66
[52] U.S. Cl. ..................................... 585/467
[58] Field of Search ........................... 585/467

[56] References Cited

U.S. PATENT DOCUMENTS

| | | | |
|---|---|---|---|
| 4,439,409 | 3/1984 | Puppe et al. | 423/328 |
| 4,859,648 | 8/1989 | Landis et al. | 502/242 |
| 4,954,325 | 9/1990 | Rubin et al. | 423/328 |
| 4,962,256 | 10/1990 | Le et al. | 585/467 |
| 4,992,606 | 12/1991 | Kushnerick et al. | 585/467 |
| 5,019,670 | 5/1991 | Le et al. | 585/467 |
| 5,026,933 | 6/1991 | Blain et al. | 585/7 |
| 5,034,563 | 7/1991 | Ashjian et al. | 585/455 |

*Primary Examiner*—Asok Pal
*Assistant Examiner*—P. Achutamurthy
*Attorney, Agent, or Firm*—Alexander J. McKillop; Dennis P. Santini; Edward F. Kenehan, Jr.

[57] ABSTRACT

Long chain alkyl aromatic compounds are prepared by alkylating an alkylatable aromatic compound with a long chain alkylating agent in the presence of catalyst comprising a synthetic porous MCM-36 material.

20 Claims, 2 Drawing Sheets

PROCESS FOR PREPARING LONG CHAIN ALKYLAROMATIC COMPOUNDS

CROSS-REFERENCE TO RELATED APPLICATIONS

This application is related to copending U.S. application Ser. No. 07/811,360, filed Dec. 20, 1991, which is a continuation-in-part of copending U.S. application Ser. No. 07/776,718, now abandoned filed Oct. 15, 1991, which is a continuation of U.S. application Ser, No. 07/640,330, filed Jan. 11, 1991, now abandoned.

BACKGROUND

The present invention relates to a process for preparing long chain alkyl aromatic compounds by alkylating an aromatic compound with a relatively long chain alkylating agent employing a particular synthetic porous MCM-36 material as alkylation catalyst.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

The alkylation of aromatic hydrocarbons with an olefin in the presence of a zeolite having uniform pore openings of from about 6 to about 15 Angstrom units is described in U.S. Pat. No. 2,904,607. U.S. Pat. No. 3,251,897 describes the alkylation of aromatic hydrocarbons in the presence of X- or Y-type zeolites, specifically such type zeolites wherein the cation is a rare earth metal species and/or hydrogen. U.S. Pat. Nos. 3,751,504 and 3,751,506 describe the vapor phase alkylation of aromatic hydrocarbons with olefins, e.g., benzene with ethylene, in the presence of a catalyst comprising, for example, ZSM-5.

U.S. Pat. Nos. 3,631,120 and 3,641,177, describe a liquid phase process for the alkylation of aromatic hydrocarbons with olefins in the presence of certain zeolites.

U.S. Pat. Nos. 4,301,316 and 4,301,317 disclose the use of such zeolites as ZSM-4, ZSM-20, ZSM-38, mazzite, Linde Type L and zeolite Beta to catalyze the alkylation of benzene with relatively long chain olefins to produce long chain alkylbenzenes.

U.S. Pat. No. 4,962,256 describes an alkylation process utilizing, as a catalyst, a zeolite designated as MCM-22. In this process, aromatics are alkylated with long-chain olefins.

SUMMARY

There is provided a process for preparing long chain alkyl aromatic compounds which comprises contacting at least one alkylatable aromatic compound with at least one alkylating agent possessing an alkylating aliphatic group having at least six carbon atoms under alkylation reaction conditions and in the presence of an alkylation catalyst to provide an alkylated aromatic product possessing at least one alkyl group derived from said alkylating agent, said catalyst comprising a synthetic porous MCM-36 material.

There is also provided a process for alkylating an alkylatable polynuclear aromatic hydrocarbon which comprises contacting the alkylatable polynuclear aromatic hydrocarbon with an olefinic alkylating agent having at least about 6 carbon atoms under alkylation reaction conditions and in the presence of an alkylation catalyst comprising a synthetic porous MCM-36 material.

EMBODIMENTS

Figure 1:
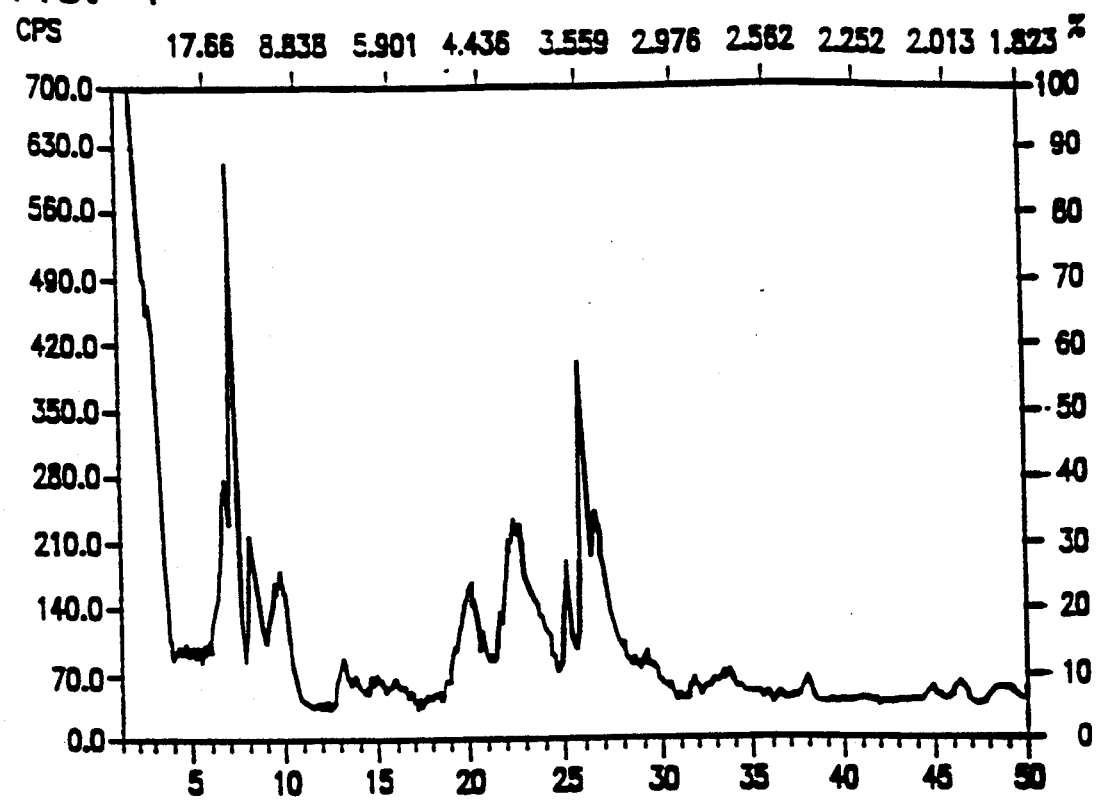
FIG. 1 is an X-ray diffraction pattern of an as-synthesized form of a layered material which may be swollen and pillared.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a hetero atom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, toluene, xylene, naphthalene, anthracene, naphthacene, perylene, coronene, phenanthrene, and alkyl-substituted derivatives of these aromatic hydrocarbons. Generally the alkyl groups which can be present as substituents on the aromatic compound contain from one to about 22 carbon atoms and preferably from about one to eight carbon atoms, and most preferably from about one to four carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such product are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate containing substantial quantities of benzene, toluene and/or xylene constitutes a particularly useful feed for the alkylation process of this invention.

The alkylating agents which are useful in the process of this invention generally include any aliphatic or aromatic organic compound having one or more available alkylating aliphatic groups capable of reaction with the alkylatable aromatic compound. The alkylatable group itself should have at least about 6 carbon atoms, preferably at least about 8, and still more preferably at least about 12 carbon atoms. Examples of suitable alkylating agents are olefins such as hexenes, heptenes, octenes, nonenes, decenes, undecenes, dodecenes, and the like; alcohols (inclusive of monoalcohols, dialcohols, trialcohols, etc.) such as hexanols, heptanols, octanols, nonanols, decanols, undecanols and dodecanols; and alkyl halides such as hexyl chlorides, octyl chlorides, dodecyl chlorides; and, higher homologs of the foregoing. Branched alkylating agents, especially oligomerized olefins such as the trimers, tetramers, pentamers, etc., of light olefins such as ethylene, propylene, the butylenes, etc., are also useful herein. Olefin oligomers described in U.S. Pat. No. 5,026,933 may be used as alkylating agents in the present process.

The alkylaromatic products produced by the present process are useful as synthetic lubricants. More particularly, alkylaromatic fluids have been proposed for use as certain types of functional fluids where good thermal and oxidative stability are required. For example, U.S. Pat. No. 4,714,794 (Yoshida) describes the monoalkylated naphthalenes as having excellent thermal and oxidative stability, low vapor pressure and flash point, good fluidity and high heat transfer capacity and other properties which render them suitable for use as thermal medium oils. The use of a mixture of monoalkylated and polyalkylated naphthalenes as a base for synthetic functional fluids is described in U.S. Pat. No. 4,604,491 (Dressler) and Pellegrini U.S. Pat. Nos. 4,211,655 and 4,238,343 describe the use of alkylaromatics as transformer oils. Properties of alkylated naphthalene lubricants are further discussed in U.S. Pat. No. 5,034,563.

Alkylated benzenes prepared by the present process are useful as synthetic lubricants and as intermediates for the preparation of detergents. More particularly, the alkylbenzenes prepared by the above-discussed alkylation process are useful as intermediates for the production of alkylphenylsulfonates, which are useful as detergents or surfactants. Processes for sulfonating alkylbenzenes are described in U.S. Pat. No. 4,298,547. More particularly, alkylbenzenes may be converted to alkylphenylsulfonates by sulfonation of the aromatic ring with sulfuric acid. The reaction is well known in the art and is commonly carried out by contacting the organic compound with sulfuric acid at temperatures of from about $-70°$ C. to about $+60°$ C. Detailed descriptions of specific commercial processes abound in the literature. See, for instance, W. L. Faith et al., INDUSTRIAL CHEMICALS, 3rd ed., p. 60–62 (1966). Those skilled in the field need only refer to the conventional literature for instruction on how to carry out such reactions.

MCM-36 and methods for its preparation are described in the aforementioned U.S. application Ser. No. 07/811,360, filed Dec. 20, 1991, the entire disclosure of which is expressly incorporated herein by reference.

MCM-36 may be prepared from an intermediate material which is crystallized in the presence of a hexamethyleneimine directing agent and which, if calcined, without being swollen would be transformed into a material having an X-ray diffraction pattern as shown in Table 1.

TABLE 1

| Interplanar d-Spacing (A) | Relative Intensity $I/I_o \times 100$ |
|---|---|
| 30.0 ± 2.2 | w-m |
| 22.1 ± 1.3 | w |
| 12.36 ± 0.2 | m-vs |
| 11.03 ± 0.2 | m-s |
| 8.83 ± 0.14 | m-vs |
| 6.86 ± 0.14 | w-m |
| 6.18 ± 0.12 | m-vs |
| 6.00 ± 0.10 | w-m |
| 5.54 ± 0.10 | w-m |
| 4.92 ± 0.09 | w |
| 4.64 ± 0.08 | w |
| 4.41 ± 0.08 | w-m |
| 4.25 ± 0.08 | w |
| 4.10 ± 0.07 | w-s |
| 4.06 ± 0.07 | w-s |
| 3.91 ± 0.07 | m-vs |
| 3.75 ± 0.06 | w-m |
| 3.56 ± 0.06 | w-m |
| 3.42 ± 0.06 | vs |
| 3.30 ± 0.05 | w-m |
| 3.20 ± 0 05 | w-m |
| 3.14 ± 0.05 | w-m |
| 3.07 ± 0.05 | w |
| 2.99 ± 0.05 | w |
| 2.82 ± 0.05 | w |
| 2.78 ± 0.05 | w |
| 2.68 ± 0.05 | w |
| 2.59 ± 0.05 | w |

The values in this Table and like tables presented hereinafter were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Tables 1-8, the relative intensities are given in terms of the symbols w=weak, m=medium, s=strong and vs=very strong. In terms of intensities, these may be generally designated as follows:

| | |
|---|---|
| w = | 0–20 |
| m = | 20–40 |
| s = | 40–60 |
| vs= | 60–100 |

The material having the X-ray diffraction pattern of Table 1 is known as MCM-22 and is described in U.S. Pat. No. 4,954,325, the entire disclosure of which is incorporated herein by reference. This material can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10–80 | 10–60 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In the synthesis method for preparing the material having the X-ray diffraction pattern of Table 1, the source of $YO_2$ must be comprised predominately of solid $YO_2$, for example at least about 30 wt. % solid $YO_2$ in order to obtain the desired crystal product. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method taught in U.S. Pat. 4,439,409. If another source of oxide of silicon e.g., Q-Brand (a sodium silicate comprised of about 28.8 wt. % $SiO_2$, 8.9 wt. % $Na_2O$ and 62.3 wt. % $H_2O$) is used, crystallization yields little or none of the crystalline material having the X-ray diffraction pattern of Table 1. Impurity phases of other crystal structures, e.g., ZSM-12, are prepared in the latter circumstance. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the crystalline material having the X-ray diffraction pattern of Table 1 can be carried out at either static or stirred conditions in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g., from about 24 hours to about 60 days. Thereafter, the crystals are separated from the liquid and recovered.

The organic directing agent for use in synthesizing the present crystalline material from the above reaction mixture may be hexamethyleneimine which has the following structural formula:

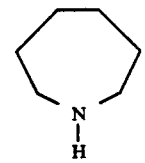

Other organic directing agents which may be used include 1,4-diazacycloheptane, azacyclooctane, aminocyclohexane, aminocycloheptane, aminocyclopentane, N,N,N-trimethyl-1-adamantanammonium ions, and N,N,N-trimethyl-2-adamantanammonium ions. In general, the organic directing agent may be selected from the group consisting of heterocyclic imines, cycloalkyl amines and adamantane quaternary ammonium ions.

It should be realized that the reaction mixture components can be supplied by more than one source. The reaction mixture can be prepared either batchwise or continuously. Crystal size and crystallization time of the crystalline material will vary with the nature of the reaction mixture employed and the crystallization conditions.

Synthesis of crystals may be facilitated by the presence of at least 0.01 percent, e.g., 0.10 percent or 1 percent, seed crystals (based on total weight) of crystalline product.

The crystalline material having the X-ray diffraction pattern of Table 1 passes through an intermediate stage. The material at this intermediate stage has a different X-ray diffraction pattern than that set forth in Table 1. It has further been discovered that this intermediate material is swellable with the use of suitable swelling agents such as cetyltrimethylammonium compounds, e.g., cetyltrimethylammonium hydroxide. However, when this swollen intermediate material is calcined, even under mild conditions, whereby the swelling agent is removed, the material can no longer be swollen with such swelling agent. By way of contrast it is noted that various layered silicates such as magadiite and kenyaite may be swellable with cetyltrimethylammonium compounds both prior to and after mild calcination.

The present swollen products may have relatively high interplanar distance (d-spacing), e.g., greater than about 6 Angstrom, e.g., greater than about 10 Angstrom and even exceeding 30 Angstrom. These swollen materials may be converted into pillared materials. These pillared materials, particularly silica pillared materials, may be capable of being exposed to severe conditions such as those encountered in calcining, e.g., at temperatures of about 450° C. for about two or more hours, e.g., four hours, in nitrogen or air, without significant decrease, e.g., less than about 10%, in interlayer distance.

The material having the X-ray diffraction pattern of Table 1, when intercepted in the swellable, intermediate state, prior to final calcination, may have the X-ray diffraction pattern shown in Table 2.

TABLE 2

| d(A) | $I/I_o$ |
|---|---|
| 13.53 ± 0.2 | m-vs |
| 12.38 ± 0.2 | m-vs |
| 11.13 ± 0.2 | w-s |
| 9.15 ± 0.15 | w-s |
| 6.89 ± 0.15 | w-m |
| 4.47 ± 0.10 | w-m |
| 3.95 ± 0.08 | w-vs |
| 3.56 ± 0.06 | w-m |
| 3.43 ± 0.06 | m-vs |
| 3.36 ± 0.05 | w-s |

An x-ray diffraction pattern trace for an example of such an as-synthesized, swellable material is shown in FIG. 1. A particular example of such an as-synthesized, swellable material is the material of Example 1 of the aforementioned U.S. Pat. No. 4,954,325. This material of Example 1 of U.S. Pat. No. 4,954,325 has the X-ray diffraction pattern given in the following Table 3.

TABLE 3

| 2 Theta | d(A) | $I/I_o \times 100$ |
|---|---|---|
| 3.1 | 28.5 | 14 |
| 3.9 | 22.7 | <1 |
| 6.53 | 13.53 | 36 |
| 7.14 | 12.38 | 100 |
| 7.94 | 11.13 | 34 |
| 9.67 | 9.15 | 20 |
| 12.85 | 6.89 | 6 |
| 13.26 | 6.68 | 4 |
| 14.36 | 6.17 | 2 |
| 14.70 | 6.03 | 5 |
| 15.85 | 5.59 | 4 |
| 19.00 | 4.67 | 2 |
| 19.85 | 4.47 | 22 |
| 21.56 | 4.12 | 10 |

TABLE 3-continued

| 2 Theta | d(A) | $I/I_o \times 100$ |
|---|---|---|
| 21.94 | 4.05 | 19 |
| 22.53 | 3.95 | 21 |
| 23.59 | 3.77 | 13 |
| 24.98 | 3.56 | 20 |
| 25.98 | 3.43 | 55 |
| 26.56 | 3.36 | 23 |
| 29.15 | 3.06 | 4 |
| 31.58 | 2.833 | 3 |
| 32.34 | 2.768 | 2 |
| 33.48 | 2.676 | 5 |
| 34.87 | 2.573 | 1 |
| 36.34 | 2.472 | 2 |
| 37.18 | 2.418 | 1 |
| 37.82 | 2.379 | 5 |

Taking into account certain modifications, this swellable material may be swollen and pillared by methods generally discussed in the aforementioned U.S. Pat. No. 4,859,648, the entire disclosure of which is expressly incorporated herein be reference. The present modifications are discussed hereinafter and include the selection of proper swelling pH and swelling agent.

Upon being swollen with a suitable swelling agent, such as a cetyltrimethylammonium compound, the swollen material may have the X-ray diffraction pattern shown in Table 4.

TABLE 4

| d(A) | $I/I_o$ |
|---|---|
| >32.2 | vs |
| 12.41 ± 0.25 | w-s |
| 3.44 ± 0.07 | w-s |

The X-ray diffraction pattern of this swollen material may have additional lines with a d(A) spacing less than the line at 12.41±0.25, but none of said additional lines have an intensity greater than the line at the d(A) spacing of 12.41±0.25 or at 3.44±0.07, whichever is more intense. More particularly, the X-ray diffraction pattern of this swollen material may have the lines shown in the following Table 5.

TABLE 5

| d(A) | $I/I_o$ |
|---|---|
| >32.2 | vs |
| 12.41 ± 0.25 | w-s |
| 11.04 ± 0.22 | w |
| 9.28 ± 0.19 | w |
| 6.92 ± 0.14 | w |
| 4.48 ± 0.09 | w-m |
| 3.96 ± 0.08 | w-m |
| 3.57 ± 0.07 | w-m |
| 3.44 ± 0.07 | w-s |
| 3.35 ± 0.07 | w |

Even further lines may be revealed upon better resolution of the X-ray diffraction pattern. For example, the X-ray diffraction pattern may have additional lines at the following d(A) spacings (intensities given in parentheses): 16.7±4.0 (w-m); 6.11±0.24 (w); 4.05±0.08 (w); and 3.80±0.08 (w).

In the region with d<9 A, the pattern for the swollen material is essentially like the one given in Table 2 for the unswollen material, but with the possibility of broadening of peaks.

Figure 2:
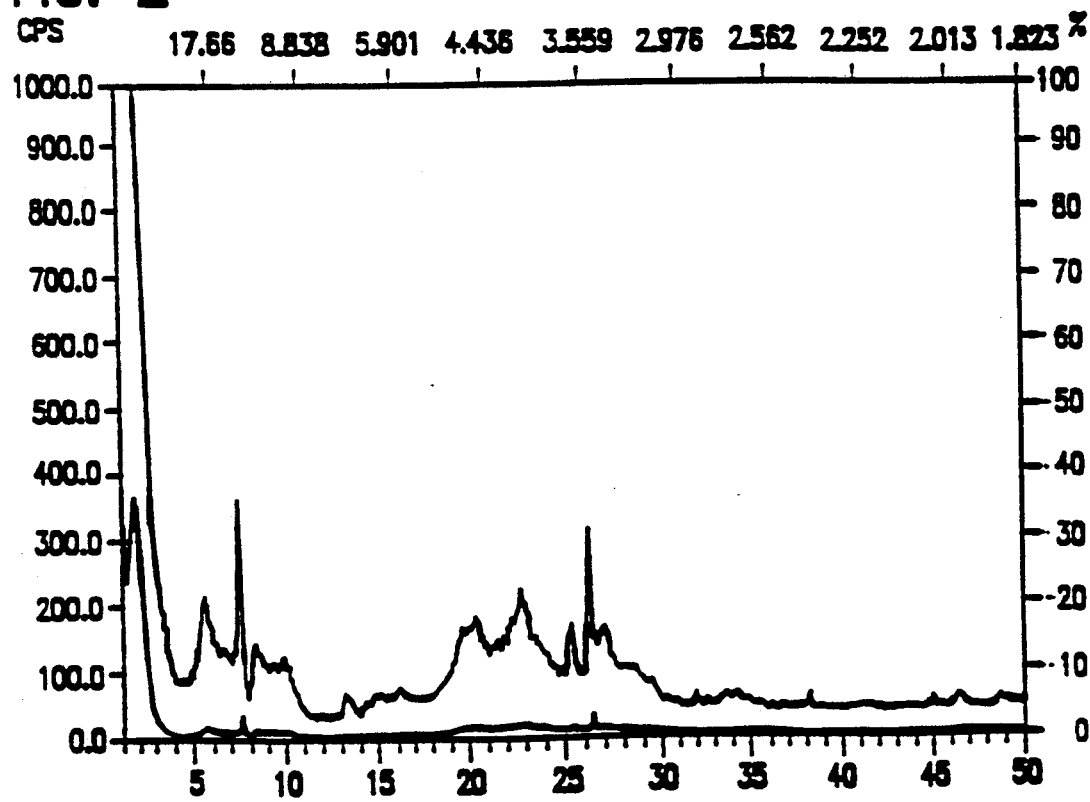
FIG. 2 is an X-ray diffraction pattern of a swollen form of the material having the X-ray diffraction pattern shown in FIG. 1.

An X-ray diffraction pattern trace for an example of such a swollen material is shown in FIG. 2. The upper profile is a 10-fold magnification of the lower profile in FIG. 2.

Upon being pillared with a suitable polymeric oxide, such as polymeric silica, the swollen material having the X-ray diffraction pattern shown in Table 4 may be converted into a material having the X-ray diffraction pattern shown in Table 6.

TABLE 6

| d(A) | $I/I_o$ |
|---|---|
| >32.2 | vs |
| 12.38 ± 0.25 | w-m |
| 3.42 ± 0.07 | w-m |

The X-ray diffraction pattern of this pillared material may have additional lines with a d(A) spacing less than the line at 12.38±0.25, but none of said additional lines have an intensity greater than the line at the d(A) spacing of 12.38±0.25 or 3.42 diffraction pattern of this pillared material may have the lines shown in the following Table 7.

TABLE 7

| d(A) | $I/I_o$ |
|---|---|
| >32.2 | vs |
| 12.38 ± 0.25 | w-m |
| 10.94 ± 0.22 | w-m |
| 9.01 ± 0.18 | w |
| 6.88 ± 0.14 | w |
| 6.16 ± 0.12 | w-m |
| 3.93 ± 0.08 | w-m |
| 3.55 ± 0.07 | w |
| 3.42 ± 0.07 | w-m |
| 3.33 ± 0.07 | w-m |

Even further lines may be revealed upon better resolution of the X-ray diffraction pattern. For example, the X-ray diffraction pattern may have additional lines at the following d(A) spacings (intensities given in parentheses): 5.59±0.11 (w); 4.42±0.09 (w); 4.11±0.08 (w); 4.04±0.08 (w); and 3.76±0.08 (w).

Figure 3:
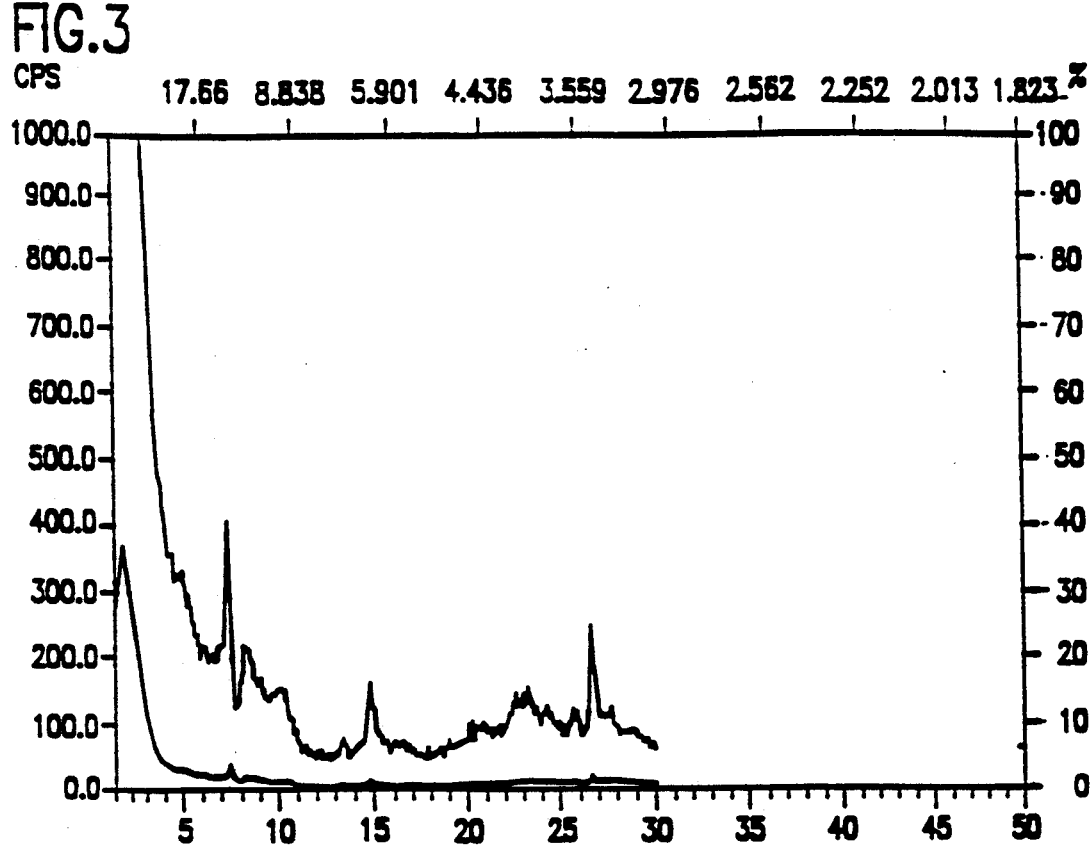
FIG. 3 is an X-ray diffraction pattern of the pillared form of the layered material having the X-ray diffraction pattern shown in FIG. 1.

An X-ray diffraction pattern trace for an example of such a pillared material is given in FIG. 3. The upper profile is a 10-fold magnification of the lower profile in FIG. 3.

If the material swollen with a suitable swelling agent is calcined without prior pillaring another material is produced. For example, if the material which is swollen but not pillared is calcined in air for 6 hours at 540° C., a very strong line at a d(A) spacing of greater than 32.2 will no longer be observed. By way of contrast, when the swollen, pillared material is calcined in air for 6 hours at 540° C., a very strong line at a d(A) spacing of greater than 32.2 will still be observed, although the precise position of the line may shift.

An example of a swollen, non-pillared material, which has been calcined, has the pattern as shown in Table 8.

TABLE 8

| 2 Theta | d(A) | $I/I_o \times 100$ |
|---|---|---|
| 3.8 | 23.3 | 12 |
| 7.02 | 12.59 | 100 |
| 8.02 | 11.02 | 20 |
| 9.66 | 9.16 | 14 |
| 12.77 | 6.93 | 7 |
| 14.34 | 6.18 | 45 |
| 15.75 | 5.63 | 8 |
| 18.19 | 4.88 | 3 |
| 18.94 | 4.69 | 3 |
| 19.92 | 4.46 | 13 broad |
| 21.52 | 4.13 | 13 shoulder |
| 21.94 | 4.05 | 18 |
| 22.55 | 3.94 | 32 |
| 23.58 | 3.77 | 16 |
| 24.99 | 3.56 | 20 |
| 25.94 | 3.43 | 61 |
| 26.73 | 3.33 | 19 |
| 31.60 | 2.831 | 3 |
| 33.41 | 2.682 | 4 |
| 34.62 | 2.591 | 3 broad |
| 36.36 | 2.471 | 1 |
| 37.81 | 2.379 | 4 |

The X-ray powder pattern shown in Table 8 is similar to that shown in Table 1 except that most of the peaks in Table 8 are much broader than those in Table 1.

Figure 4:
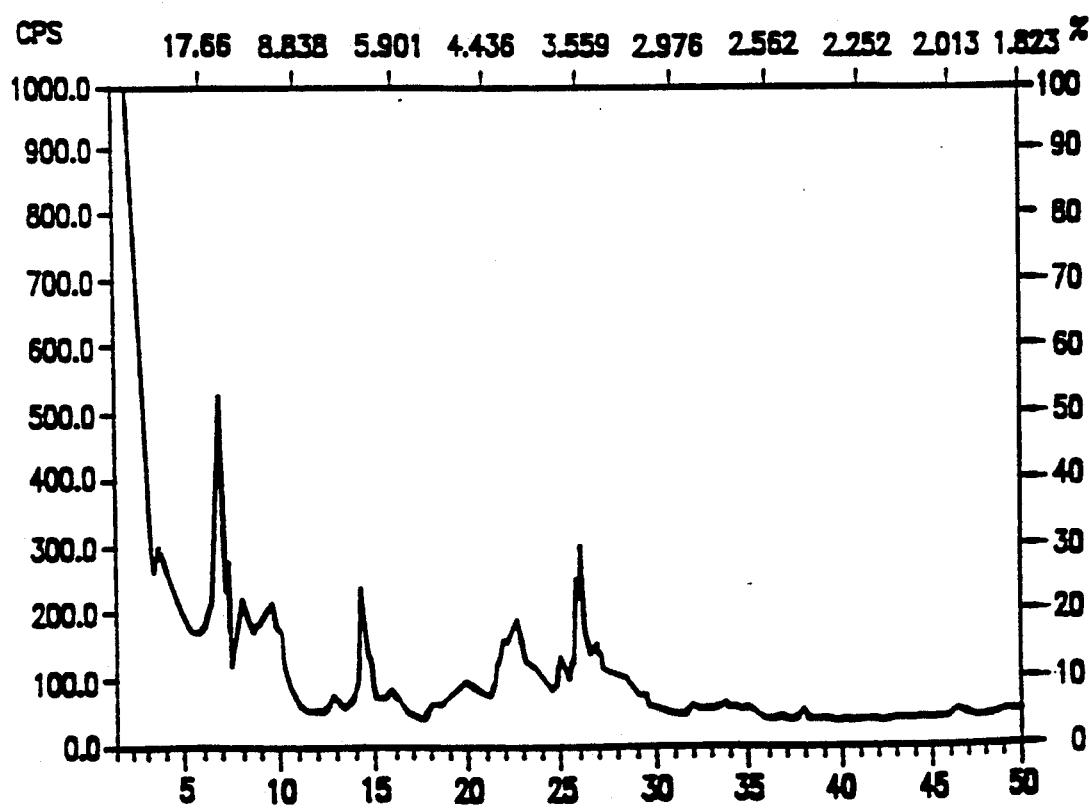
FIG. 4 is an X-ray diffraction pattern of the calcined form of the swollen material having the X-ray diffraction pattern shown in FIG. 2.

An X-ray diffraction pattern trace for an example of the calcined material corresponding to Table 8 is given in FIG. 4.

As mentioned previously, the calcined material corresponding to the X-ray diffraction pattern of Table 1 is designated MCM-22. For the purposes of the present disclosure, the pillared material corresponding to the X-ray diffraction pattern of Table 6 is designated herein as MCM-36. The swollen material corresponding to the X-ray diffraction pattern of Table 4 is designated herein as the swollen MCM-22 precursor. The as-synthesized material corresponding to the X-ray diffraction pattern of Table 2 is referred to herein, simply, as the MCM-22 precursor.

The layers of the swollen material of this disclosure may have a composition involving the molar relationship:

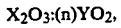

wherein X is a trivalent element, such as aluminum, boron, iron and/or gallium, preferably aluminum, Y is a tetravalent element such as silicon and/or germanium, preferably silicon, and n is at least about 5, usually from about 10 to about 150, more usually from about 10 to about 60, and even more usually from about 10 to about 40.

To the extent that the layers of the swollen MCM-22 precursor and MCM-36 have negative charges, these negative charges are balanced with cations. For example, expressed in terms of moles of oxides, the layers of the swollen MCM-22 precursor and MCM-36 may have a ratio of 0.5 to 1.5 $R_2O:X_2O_3$, where R is a monovalent cation or 1/m of a cation of valency m.

MCM-36 adsorbs significant amounts of commonly used test adsorbate materials, i.e., cyclohexane, n-hexane and water. Adsorption capacities for this pillared material, especially the silica pillared material, may range at room temperature as follows:

| Adsorbate | Capacity, Wt. Percent |
|---|---|
| n-hexane | 17-40 |
| cyclohexane | 17-40 |
| water | 10-40 | wherein cyclohexane and n-hexane sorption are measured at 20 Torr and water sorption is measured at 12 Torr.

The swellable material, used to form the swollen material of the present disclosure, may be initially treated with a swelling agent. Such swelling agents are materials which cause the swellable layers to separate by becoming incorporated into the interspathic region of these layers. The swelling agents are removable by calcination, preferably in an oxidizing atmosphere, whereby the swelling agent becomes decomposed and/or oxidized.

Suitable swelling agents may comprise a source of organic cation, such as quaternary organoammonium or organophosphonium cations, in order to effect an exchange of interspathic cations. Organoammonium cations, such as n-octylammonium, showed smaller swelling efficiency than, for example, cetyltrimethylammonium. A pH range of 11 to 14, preferably 12.5 to 13.5 is generally employed during treatment with the swelling agent.

The as-synthesized material is preferably not dried prior to being swollen. This as-synthesized material may be in the form of a wet cake having a solids content of less than 30 % by weight, e.g., 25 wt % or less.

The foregoing swelling treatment results in the formation of a layered oxide of enhanced interlayer separation depending upon the size of the organic cation introduced. In one embodiment, a series of organic cation exchanges can be carried out. For example, an organic cation may be exchanged with an organic cation of greater size, thus increasing the interlayer separation in a step-wise fashion. When contact of the layered oxide with the swelling agent is conducted in aqueous medium, water is trapped between the layers of the swollen species.

The organic-swollen species may be treated with a compound capable of conversion, e.g., by hydrolysis and/or calcination, to pillars of an oxide, preferably to a polymeric oxide. Where the treatment involves hydrolysis, this treatment may be carried out using the water already present in organic-swollen material. In this case, the extent of hydrolysis may be modified by varying the extent to which the organic-swollen species is dried prior to addition of the polymeric oxide precursor.

It is preferred that the organic cation deposited between the layers be capable of being removed from the pillared material without substantial disturbance or removal of the interspathic polymeric oxide. For example, organic cations such as cetyltrimethylammonium may be removed by exposure to elevated temperatures, e.g., calcination, in nitrogen or air, or by chemical oxidation preferably after the interspathic polymeric oxide precursor has been converted to the polymeric oxide pillars in order to form the pillared layered product.

These pillared layered products, especially when calcined, exhibit high surface area, e.g., greater than 500 $m^2/g$, and thermal and hydrothermal stability making them highly useful as catalysts or catalytic supports, for hydrocarbon conversion processes, for example, alkylation.

Insertion of the organic cation between the adjoining layers serves to physically separate the layers in such a way as to make the layered material receptive to the interlayer addition of a polymeric oxide precursor. In particular, cetyltrimethylammonium cations have been found useful. These cations are readily incorporated within the interlayer spaces of the layered oxide serving to prop open the layers in such a way as to allow incorporation of the polymeric oxide precursor. The extent of the interlayer spacing can be controlled by the size of the organoammonium ion employed.

Interspathic oxide pillars, which may be formed between the layers of the propped or swollen oxide material, may include an oxide, preferably a polymeric oxide, of zirconium or titanium or more preferably of an element selected from Group IVB of the Periodic Table (Fischer Scientific Company Cat. No. 5-702-10, 1978), other than carbon, i.e., silicon, germanium, tin and lead. Other suitable oxides include those of Group VA, e.g., V, Nb, and Ta, those of Group IIA, e.g., Mg or those of Group IIIB, e.g., B. Most preferably, the pillars include polymeric silica. In addition, the oxide pillars may include an element which provides catalytically active acid sites in the pillars, preferably aluminum.

The oxide pillars are formed from a precursor material which may be introduced between the layers of the organic "propped" species as an ionic or electrically neutral compound of the desired elements, e.g., those of Group IVB. The precursor material may be an organometallic compound which is a liquid under ambient conditions. In particular, hydrolyzable compounds, e.g., alkoxides, of the desired elements of the pillars may be utilized as the precursors. Suitable polymeric silica precursor materials include tetraalkylsilicates, e.g., tetrapropylorthosilicate, tetramethylorthosilicate and, most preferably, tetraethylorthosilicate. Suitable polymeric silica precursor materials also include quaternary ammonium silicates, e.g., tetramethylammonium silicate (i.e. TMA silicate). Where the pillars also include polymeric alumina, a hydrolyzable aluminum compound can be contacted with the organic "propped" species before, after or simultaneously with the contacting of the propped layered oxide with the silicon compound. Preferably, the hydrolyzable aluminum compound employed is an aluminum alkoxide, e.g., aluminum isopropoxide. If the pillars are to include titania, a hydrolyzable titanium compound such as titanium alkoxide, e.g., titanium isopropoxide, may be used.

After calcination to remove the organic propping agent, the final pillared product may contain residual exchangeable cations. Such residual cations in the layered material can be ion exchanged by known methods with other cationic species to provide or alter the catalytic activity of the pillared product. Suitable replacement cations include cesium, cerium, cobalt, nickel, copper, zinc, manganese, platinum, lanthanum, aluminum, ammonium, hydronium and mixtures thereof.

Particular procedures for intercalating layered materials with metal oxide pillars are described in U.S. Pat. Nos. 4,831,005; 4,831,006; and 4,929,587. The entire disclosures of these patents are expressly incorporated herein by reference. U.S. Pat. No. 4,831,005 describes plural treatments with the pillar precursor. U.S. Pat. No. 4,929,587 describes the use of an inert atmosphere, such as nitrogen, to minimize the formation of extralaminar polymeric oxide during the contact with the pillar precursor. U.S. Pat. No. 4,831,006 describes the use of elevated temperatures during the formation of the pillar precursor.

The resulting pillared products exhibit thermal stability at temperatures of 450° C. or even higher as well as substantial sorption capacities (as much as 17 to 40 wt % for $C_6$ hydrocarbon). The pillared products may possess a basal spacing of at least about 32.2Å and surface areas greater than 500 $m^2/g$.

The layered material may be subjected to thermal treatment, e.g., to decompose organoammonium ions. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience.

Prior to its use as a catalyst, MCM-36 should be subjected to thermal treatment to remove part or all of any organic constituent present therein.

MCM-36 can optionally be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be associated chemically and/or physically with the MCM-36 and/or matrix with which the MCM-36 may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the MCM-36 such as, for example, by, in the case of platinum, treating the MCM-36 with a solution containing the platinum metal-containing ion. Thus, suitable platinum compounds for this purpose include chloroplatinic acid, platinous chloride and various compounds containing the platinum amine complex.

The MCM-36, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use as a catalyst, the MCM-36 crystals may be at least partially dehydrated. This dehydration can be accomplished by heating the MCM-36 to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the MCM-36 in a vacuum but a longer time will be required to achieve a suitable degree of dehydration.

The MCM-36 can be shaped into a wide variety of particle sizes. Generally speaking, the particles can be provided in the form of a powder, a granule or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desired to incorporate the MCM-36 with another material, i.e., a binder, which is resistant to the temperatures and other conditions employed in the isoparaffin alkylation process of this invention. Suitable binder materials include active and inactive materials and synthetic or naturally occurring zeolites as well as inorganic materials such as clays, silica and/or metal oxides such as alumina. The latter can be either naturally occurring or provided in the form of gelatinous precipitates or gels including mixtures of silica and metal oxides. Use of a binder material in conjunction with MCM-36, i.e., combined therewith or present during its synthesis, which itself is catalytically active may change the conversion and/or selectivity of the catalyst. Inactive materials suitably serve as diluents to control the amount of conversion so that alkylation products can be obtained economically and in a controlled fashion without having to employ other means for controlling the rate of reaction. These materials can be incorporated into naturally occurring clays, e.g., bentonite and kaolin, to improve the crush strength of the MCM-36 under commercial alkylation operating conditions. Good crush strength is an advantageous attribute for commercial use since it prevents or delays breaking down of the catalyst into powder-like materials.

Naturally occurring clays which can be composited with MCM-36 crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with MCM-36 also include inorganic oxides, notably alumina.

Apart from or in addition to the foregoing binder materials, the MCM-36 crystals can be composited with an inorganic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may be advantageous to provide at least a part of the foregoing matrix materials in colloidal form so as to facilitate extrusion of the bound catalyst component(s).

The relative proportions of finely divided MCM-36 and inorganic oxide matrix can vary widely with the MCM-36 content ranging from about 1 to about 95 percent by weight and more usually, particularly when the composite is prepared in the form of beads, in the range of about 2 to about 80 weight percent of the composite.

The alkylation process of this invention is conducted such that the organic reactants, i.e., the alkylatable aromatic compound and the alkylating agent, are brought into contact with the catalyst composition in a suitable reaction zone such as, for example, in a flow reactor containing a fixed bed of the catalyst composition, under effective alkylation conditions. Such conditions include a temperature of from about 0° C. to about 500° C., a pressure of from about 0.2 to about 250 atmospheres, a feed weight hourly space velocity (WHSV) of from about 0.1 $hr^{-1}$ to about 500 $hr^{-1}$ and an alkylatable aromatic compound to alkylating agent mole ratio of from about 0.1:1 to about 50:1. The WHSV is based upon the weight of the catalyst composition employed, i.e., the total weight of active catalyst (and binder if present). Preferred reaction conditions include a temperature within the approximate range of from about 50° C. to about 350° C., a pressure of from about 1 to about 25 atmospheres, a WHSV of from about 0.5 $hr^{-1}$ to about 100 $hr^{-1}$ and an alkylatable aromatic compound to alkylating agent mole ratio of from about 0.5:1 to about 5:1. The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen.

The alkylation process described herein can be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

In order to more fully illustrate the alkylation process of this invention and the manner of practicing same, the following examples are presented. In examples illustrative of the synthesis of MCM-36, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the absorbent, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant.

EXAMPLE 1

A material which may be swollen and pillared was prepared as follows. Water, sodium hydroxide, sodium aluminate, silica (Ultrasil), and hexamethyleneimine (HMI) were combined in the following mole ratios:

2.5 Na$_2$O: Al$_2$O$_3$: 30 SiO$_2$:10 HMI: 580 H$_2$O.

The reaction mixture was heated in an autoclave to 143° C. for 96 hours. The X-ray diffraction pattern for this material is shown pictorially in FIG. 1.

A mixture of 150 g of the wet cake (42% solids) and 1100 ml of 29% CTMA-OH (a 29% solution of cetyltrimethylammonium chloride that was contacted with hydroxide-for-halide exchange resin-1 liter of the resin with 1.4 miliequivalent/ml exchange capacity per 3 liters of the solution) was reacted for 96 hours in a steambox. The product was filtered, washed twice with 400 ml of water and air dried overnight, yielding approximately 101 g of swollen product. Fifty grams of the swollen material was slurried with 300 g of TEOS and heated at 80° C. for 24 hours under a stream of nitrogen. After filtration and overnight drying, the product (56.60 g) was hydrolyzed in water for 4 hours, giving the pillared material (approximately 50 grams) containing 70% so ids (based upon calcination at 540° C.). A portion (44.3 grams) of the pillared material was mixed with 23.3 g of Kaiser alumina (72.5% solids) and pelletized. The pellets were exchanged four times with 1M ammonium nitrate (one hour contact followed by washing with 300 ml of water). The product was reformulated into pellets, dried at 110° C. for two hours and calcined in nitrogen for 3 hours and in air for 6 hours. Total product yield was approximately 41 grams of 65% MCM-36/35% Al$_2$O$_3$.

EXAMPLE 2

This Example demonstrates the catalytic activity of the 65% MCM-36/35% Al$_2$O$_3$ catalyst of Example 1 for alkylating benzene with alpha C$_{14}$ olefin (1:1 mole ratio). The alkylation reaction was carried out in an autoclave using 5% catalyst at 400° F. for 20 hours under a nitrogen atmosphere of 200 psig. The catalyst performance is shown in Table 9.

TABLE 9

| Catalyst | MCM-36 |
|---|---|
| Conversion. Wt % | |
| Benzene | 97 |
| Alpha C$_{14=}$ | 97 |
| Alkylated Benzene Yield, Wt % | 97 |
| Product Distribution, Wt % | |
| Mono-Alkylated Benzene | 81 |
| Di-Alkylated Benzene | 19 |

The results indicate that MCM-36 achieved a near complete conversion of the feed (97 wt % conversion of benzene and olefin). In addition, MCM-36 did not promote the formation of undesirable olefin dimers.

What is claimed is:

1. A process for preparing long chain aromatic compounds which comprises contacting at least one alkylatable aromatic compound with at least one alkylating agent possessing an alkylating aliphatic group having at least six carbon atoms under alkylation reaction conditions and in the presence of an alkylation catalyst to provide an alkylated aromatic product possessing at least one alkyl group derived from said alkylating agent, said catalyst comprising a synthetic porous crystalline MCM-36 material, said MCM-36 material being a pillared material having the X-ray diffraction pattern of Table 6.

2. A process according to claim 1, wherein the layers of the MCM-36 have a composition comprising the molar relationship $$X_2O_3:(n)YO_2,$$

wherein n is at least about 5, X is a trivalent element and Y is a tetravalent element, said MCM-36 having the X-ray diffraction pattern of Table 7.

3. A process according to claim 2, wherein X is selected from the group consisting of aluminum, boron, gallium and combinations thereof and Y is selected from the group consisting of silicon, germanium and combinations thereof.

4. A process according to claim 2, wherein X comprises aluminum and Y comprises silicon.

5. A process according to claim 1, wherein said synthetic porous crystalline material is combined with a material matrix.

6. A process according to claim 5, wherein said matrix material is a silica or alumina-containing material.

7. A process according to claim 5, wherein the catalyst is provided in the form of extrudate, beads or fluidizable microspheres.

8. A process according to claim 1, wherein the alkylating aliphatic group contains at least about 8 carbon atoms.

9. A process according to claim 1, wherein the alkylating aliphatic group contains at least about 12 carbon atoms.

10. A process according to claim 1, wherein the alkylating agent is an olefin.

11. A process according to claim 1, wherein the alkylating agent is an alcohol.

12. A process according to claim 1, wherein the alkylating agent is an alkyl halide.

13. A process according to claim 1, wherein the alkylatable aromatic compound is selected from the group consisting of benzene, xylene, toluene and 1,2,3,5-tetramethylbenzene.

14. A process according to claim 1, wherein the alkylatable aromatic compound is selected from the group consisting of naphthalene, anthracene, naphthacene, perylene, coronene and phenanthrene.

15. A process according to claim 1, wherein the alkylation reaction conditions include a temperature of from about 0° C. to about 500° C., a pressure of from about 0.2 to about 250 atmospheres, an WHSV of from about 0.1 hr$^{-1}$ to 500 hr$^{-1}$ and an alkylatable aromatic compound to alkylating agent mole ratio of from about 0.1:1 to 50:1.

16. A process according to claim 1, wherein the alkylation reaction conditions include a temperature of from about 50° C. to 350° C., a pressure of from about 1 to about 25 atmospheres, a WHSV of from about 0.5 hr$^{-1}$ to about 100 hr$^{-1}$ and an alkylatable aromatic compound to alkylating agent mole ratio of from about 0.5:1 to about 5:1.

17. A process for alkylating an alkylatable polynuclear aromatic hydrocarbon which comprises contacting the alkylatable polynuclear aromatic hydrocarbon with an olefinic alkylating agent having at least about 6 carbon atoms under alkylation reaction conditions and in the presence of an alkylation catalyst comprising a synthetic porous crystalline MCM-36 material, said MCM-36 material being a pillared material having the X-ray diffraction pattern of Table 6.

18. A process according to claim 17, wherein the polynuclear aromatic hydrocarbon is selected from the group consisting of naphthalene, anthracene, perylene, coronene and phenanthrene.

19. A process according to claim 18, wherein the olefinic alkylating agent contains at least about 12 carbon atoms.

20. A process according to claim 17, wherein the layers of the MCM-36 have a composition comprising the molar relationship

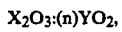

$X_2O_3:(n)YO_2,$ wherein n is at least about 5, X is a trivalent element and Y is a tetravalent element, said MCM-36 having the X-ray diffraction pattern of Table 7.

* * * * *